(12) United States Patent
Zeng (10) Patent No.: US 7,383,077 B2
(45) Date of Patent: Jun. 3, 2008

(54) IN VIVO RAMAN ENDOSCOPIC PROBE

(75) Inventor: Haishan Zeng, Vancouver (CA)

(73) Assignee: British Colombia Cancer Agency (CA)

( * ) Notice: Subject to any disclaimer, the term of this patent is extended or adjusted under 35 U.S.C. 154(b) by 917 days.

(21) Appl. No.: 10/761,703

(22) Filed: Jan. 21, 2004

(65) Prior Publication Data

US 2004/0152992 A1 Aug. 5, 2004

Related U.S. Application Data

(60) Provisional application No. 60/441,566, filed on Jan. 21, 2003.

(51) Int. Cl.
*A61B 5/00* (2006.01)
(52) U.S. Cl. .................. 600/473; 600/160
(58) Field of Classification Search ........ 600/475–480, 600/473, 160, 162; 356/301, 318, 326, 331
See application file for complete search history.

(56) References Cited

U.S. PATENT DOCUMENTS

| 5,521,703 | A | * | 5/1996 | Mitchell | ............. | 356/301 |
|---|---|---|---|---|---|---|
| 6,069,689 | A | | 5/2000 | Zeng et al. | | |
| 6,486,948 | B1 | | 11/2002 | Zeng | | |
| 2001/0012429 | A1 | | 8/2001 | Wach et al. | | |

FOREIGN PATENT DOCUMENTS

WO WO 98/00057 1/1998
WO WO 03/087793 10/2003

OTHER PUBLICATIONS

Mahadevan-Jensen et al., "Raman Spectroscopy for the Detection of Cancers and Precancers", Journal Of Biomedical Optics, vol. 1, No. 1, p. 31-70, Jan. 1996.
Shim et al., "In vivo Near-infrared Raman Spectroscopy: Demonstration of Feasibility During Clinical Gastrointestinal Endoscopy", Photochemistry and Photobiology, vol. 72, No. 1, p. 146-150, 2000.
Utzinger et al., "Near-infrared Raman Spectroscopy for in vivo Detection of Cervical Precancers", Applied Spectroscopy, vol. 55, No. 8, p. 955-959, 2001.

(Continued)

*Primary Examiner*—Ruth S. Smith
*Assistant Examiner*—Justin Chao
(74) *Attorney, Agent, or Firm*—Trexler, Bushnell, Giangiorgi, Blackstone & Marr Ltd.

(57) ABSTRACT

An apparatus for in vivo, endoscopic laser Raman spectroscopy probe and methods for its use are described. The probe comprises a fiber bundle assemble small enough to fit through an endoscope instrument channel, a novel combination of special coatings to the fiber bundle assembly, including a short-pass filter on the illumination fiber and a long-pass filter on the collection fiber bundle, a novel filter adapter comprising collimating lenses, focusing lenses, a band-pass filter, and a notch filter, and a round-to-parabolic linear array fiber bundle. The apparatus further comprises a laser to deliver illumination light and a spectrometer to analyze Raman-scattered light from a sample. The analysis of Raman spectra from in vivo measurements can discover molecular and structural changes associated with neoplastic transformations and lead to early diagnosis and treatment of cancer.

67 Claims, 6 Drawing Sheets

OTHER PUBLICATIONS

Mahadevan-Jensen, "Development of a Fiber Optic Probe to Measure NIR Raman Spectra of Cervical Tissue In Vivo", Photochem. Photobiol. 68: 427-431, 1998.

Kaminaka, "Near-infrared Raman Spectroscopy of Human Lung Tissues: Possibility of Molecular-level Cancer Diagnosis", J. Raman Spectrosc. 32: 139-141, 2001.

Kaminaka, "Near-infrared Multichannel Raman Spectroscopy Toward Real-time In Vivo Cancer Diagnosis", J. Raman Spectrosc. 33: 498-502, 2002.

Shim, "The Effects of Ex Vivo Handling Procedures on the Near-Infrared Raman Spectra of Normal Mammalian Tissues", Photochem. Photobiol., 63: 662-671, 1996.

Huang, Near-InfraredRaman Spectroscopy for Optical Diagnosis of Lung Cancer, 107 Int. J. Cancer 1047-52 (2003).

Huang, Rapid near-infrared Raman spectroscopy system for real-time in vivo skin measurements, 26 Opt. Lett. 1782 (2001).

International Search Report dated May 6, 2004 which issued in connection with a corresponding PCT application.

* cited by examiner

IN VIVO RAMAN ENDOSCOPIC PROBE

CROSS-REFERENCE

This application claims priority from provisional application No. 60/441,566, filed on Jan. 21, 2003.

BACKGROUND OF THE INVENTION

Lung cancer is the leading cause of death from cancer in North America, and it has the second most common cancer incidence among both men and women. One in 11 Canadian men will develop lung cancer, and 1 in 12 will die from this condition, while one in 19 Canadian women will develop lung cancer, and 1 in 22 will die from this disease. Lung cancer also results in the most lost years of life due to cancer death in both men and women. The best outcome of lung cancer treatment is achieved when the lesion is discovered in the pre-invasive stage, which is also commonly referred as carcinoma in situ (CIS).

Early and accurate diagnosis of lung cancer offers a better chance of cure, results in the use of less radical treatment methods, and reduces the cost of treatment. The five-year survival for all stages of lung cancer is only 11-14 percent, while for Stage I it is 42 to 47 percent. Under optimal conditions, survival can be even higher. However, with respect to currently available lung imaging techniques, lung cancer is generally asymptomatic until it has reached an advanced stage, when the treatment outcome is poor. In particular, very early lung cancers are difficult to detect and localize by conventional white-light endoscopy since these cancers are only a few cell layers thick and LIP to a few millimeters in surface diameter, producing insufficient changes to make them visible under white light illumination. In the lung, only about 30 percent of CIS lesions are visible by conventional white-light bronchoscopy.

In the past decade, tissue autofluorescence imaging has been successfully used to improve the early detection of lung cancers. However, fluorescence endoscopy technology (developed at B.C. Cancer Agency and also referred as "LIFE" technology) has less optimal specificity for lung cancer detection (66 percent for LIFE compared to 90 percent for conventional white light bronchoscopy) although it improved the sensitivity from 25 percent for white light bronchoscope to 67 percent for LIFE. There is still much room for improvement in the diagnostic accuracy.

Recently, we have performed Raman spectroscopy measurements on fresh biopsy bronchial tissue samples and found significant spectral differences between normal and malignant lung tissues, demonstrating the potential of Raman spectroscopy for in vivo lung cancer detection.

In contrast to fluorescence technology, Laser-Raman spectroscopy probes molecular vibrations and gives very specific, fingerprint-like spectral features and has high accuracy for differentiation of malignant tissues from benign tissues. Raman spectroscopy can also be used to identify the structural and compositional differences on proteins and genetic materials between malignant lung cancers, their pre-cursers, and normal lung tissues. This knowledge will lead to better understanding, on the biochemical bases, of the evolution process of lung cancers from benign to malignancy. The biochemical information obtained from in vivo Raman measurements may also be helpful for predicting the malignancy potential of pre-invasive and invasive lung cancers. The objective of this invention is to develop a miniaturized laser-Raman probe, which can go through the instrument channel of a bronchoscope to perform Raman spectroscopy measurements of the bronchial tree in vivo. A further objective is to enable the application of Raman spectroscopy for in vivo lung cancer detection and evaluation, therefore, improve the specificity of lung cancer detection and the overall detection accuracy when combined with fluorescence endoscopy technology.

When monochromatic light strikes a sample, almost all the observed light is scattered elastically (Rayleigh scattering) with no change in energy (or frequency). A very small portion of the scattered light, about 1 in $10^8$, is inelastically scattered (Raman scattering) with a corresponding change in frequency. The difference between the incident and scattered frequencies corresponds to an excitation of the molecular system, most often excitation of vibrational modes. By measuring the intensity of the scattered photons as a function of the frequency difference, a Raman spectrum is obtained. Raman peaks are typically narrow (a few wavenumbers) and in many cases can be attributed to the vibration of specific chemical bonds (or normal mode dominated by the vibration of a single functional group) in a molecule. As such, it is a "fingerprint" for the presence of various molecular species and can be used for both qualitative identification and quantitative determination.

In recent years, Raman spectroscopy has been investigated for in vitro diagnosis of malignancies in various organs (e.g., brain, breast, bladder, colon, larynx, cervix, and skin). These studies show that features of tissue Raman spectra can be related to the molecular and structural changes associated with neoplastic transformations. A sensitivity and specificity of 82 percent and 92 percent respectively for differentiating between cervical precancerous and other tissues in vitro have been reported. Mahadevan-Jansen, *Raman spectroscopy for the detection of cancers and precancers*, J BIOMED. OPT. 1, 31-70, 1996.

In vivo NIR Raman measurements have also been reported in the cervix, colon, esophagus, and the skin. Mahadevan-Jansen, *Development of a fiber optic probe to measure NIR Raman spectra of cervical tissue in vivo*, PHOTOCHEM. PHOTOBIOL. 68: 427-431, 1998; Shim, *In vivo near-infrared Raman spectroscopy: demonstration of feasibility during clinical gastrointestinal endoscopy*, PHOTOCHEM. PHOTOBIOL. 72: 146-150, 2000; Huang, *Rapid near-infrared Raman spectroscopy system for real-time in vivo skin measurements*, OPT. LETT. 26: 1782-1784, 2001; Utzinger, *Near-infrared Raman spectroscopy for in vivo detection of cervical precancers*, APPL. SPECTROSC. 55:955-959, 2001.

Shim et al. have shown differences for in vivo Raman spectra among normal, precancerous, and cancerous esophageal and gastric tissues. Raman spectroscopy of lung tissues, however, has only been reported on formalin-fixed parenchyma lung diseases, which provide very limited guidance to in vivo applications due to the adverse effect of formalin fixation on tissue Raman spectra. Kaminaka, *Near-infrared Raman spectroscopy of human lung tissues: possibility of molecular-level cancer diagnosis*, J. RAMAN SPECTROSC. 32:139-141, 2001; Kaminaka, *Near-infrared multichannel Raman spectroscopy toward real-time in vivo cancer diagnosis*, J. RAMAN SPECTROSC. 33:498-502, 2002; Shim, *The effects of ex vivo handling procedures on the near-infrared Raman spectra of normal mammalian tissues*, PHOTOCHEM. PHOTOBIOL. 63: 662-671, 1996.

The development of an in vivo tissue Raman probe is technically challenging due to the weak Raman signal of tissue, interference from tissue fluorescence and spectral contamination caused by the background Raman and fluorescence signals generated in the fiber itself. Most probes published in literature and commercial products are larger than 10 mm in diameter, and therefore are not suitable for endoscopy applications. The instrument channel of commonly-used bronchoscopes are 2.2 mm (for example, Olympus BF-20, BF-40).

To date, the only endoscopic probe utilized for in vivo measurements is the Enviva Raman probe manufactured by Visionex, Inc., Atlanta, Ga. However, the company was dissolved two years ago; therefore, the probe is no longer commercially available. That probe consisted of a central delivery fiber (400 μm core diameter) surrounded by seven collection fibers (300 μm core diameter). It incorporated LP filters in the collection fibers and a BP filter in the delivery fiber. The main disadvantages of that probe are that (1) only seven collection fibers were used, which cannot fill the full vertical height of the CCD sensor in the spectrometer; therefore, it was unable to gain the maximum sensitivity; and (2) the size of the collection fibers was big (300 μm), leading to poor spectral resolution (>20 $cm^{-1}$).

BRIEF SUMMARY OF THE INVENTION

The present invention comprises a novel endoscopic Raman probe. In the preferred embodiment, the probe comprises 58 collection fibers (100 μm core diameter), which will fill the CCD full vertical height and achieve spectral resolution of 8 $cm^{-1}$. However, a probe comprising a smaller or larger number of collection fibers will be appropriate for use with a spectrometer having a different sized CCD. The novel probe will also preserve the round-to-parabolic linear array configuration of the Raman probe for in vivo skin measurements, as described in U.S. Pat. No. 6,486,948. The probe of the present invention therefore, will achieve similar superior S/N ratios and a short integration time of a few seconds or sub-seconds for each Raman spectral measurement.

The present invention utilizes the state-of-art fiber optic technology, filtering technology, laser machining technology, and the existing rapid Raman spectroscopy system, to build a miniaturized laser-Raman probe for use in an endoscope. In the preferred embodiment, the probe will pass through the instrument channel of a bronchoscope and acquire Raman spectra from the bronchial tree in vivo. In other embodiments, the probe will be used with other endoscopes. In other embodiments, the laser-Raman probe will be integrated with a spectrometer to perform Raman spectroscopy for analysis of the iii vivo tissue under examination.

The preferred embodiment of the invention comprises:
1. A special probing fiber bundle assembly of about 65 cm long and 1.9 mm in diameter to pass though the endoscope instrument channel and to be in contact with the tissue to provide illumination and to collect Raman scattering photons;
2. Special coatings applied to the distal end of the probing fiber bundle assembly to produce a short-pass (SP) filter on the single illumination fiber and a long-pass (LP) filter on the collection fiber bundle;
3. A novel filter adapter to accommodate a high quality band-pass (BP) filter to pass through only the laser light transmitted through the illumination fiber and also to accommodate a notch filter to block the back-scattered laser light from passing through the collection fiber bundle;
4. A round-to-parabolic linear array fiber bundle using laser-machining technology to relay the collected Raman signal to the Raman spectrometer for spectral analysis. This special fiber bundle serves to correct the spectrograph image aberration and improve signal to noise (S/N) ratio;
5. Integration of the probing fiber bundle assembly, the filter adapter, the illumination fiber, and the round-to-parabolic linear array fiber bundle to form the endoscopic laser-Raman probe.

This embodiment can be used in an endoscope. In another embodiment, the invention comprises the probe described above used in conjunction with a spectrometer capable of performing Raman spectral analysis.

BRIEF DESCRIPTION OF DRAWINGS

The foregoing and other objects, features, and advantages of the invention will be apparent from the following descriptions of preferred embodiments and drawings illustrating principals of the invention and its uses.

FIG. 3b is an image of the same 100 μm slit on a CCD through a spectrograph as in FIG. 3a, corrected compared to the image of FIG. 3a.

FIG. 4 is a graphical representation for the curve observed in FIG. 3a.

DETAILED DESCRIPTION OF THE INVENTION

Figure 1:
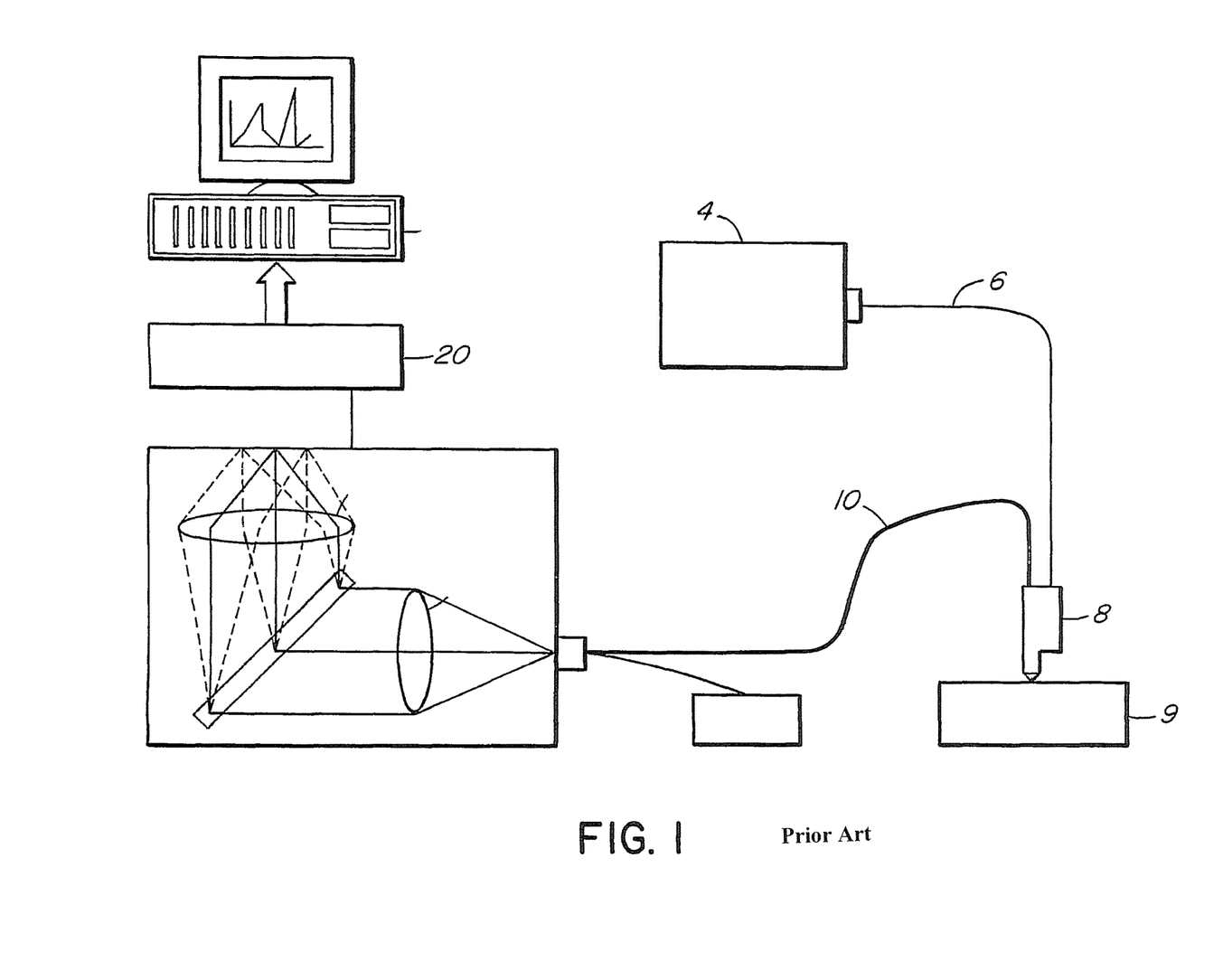
FIG. 1 is a schematic block diagram of the rapid Raman spectrometer system for in vivo skin measurements.

We have successfully built a rapid Raman spectroscopy system, which can obtain a Raman spectrum from in vivo skin in less than one second. This system is described and claimed in U.S. Pat. No. 6,486,948, the disclosure of which is incorporated by reference. FIG. 1 shows the block diagram of the system. It consists of an external cavity-stabilized diode laser 4 (785 nm, 300 mW; Model 8530, SDL), a transmissive imaging spectrograph 2 (HoloSpec-f/2.2-NIR, Kaiser), a NIR-optimized, back-illuminated, deep-depletion, CCD detector 20 (LN/CCD-1024EHRB, Princeton Instruments), and a specially-designed Raman probe 8. The laser 4 is coupled to the Raman probe 8 via a 200-μm core-diameter fiber 6. The CCD 20 consists of 1024×256 pixels (27 μm×27 μm) and allowed vertical binning for improved detection sensitivity. The whole system was packed onto a movable cart for outpatient clinical data acquisition.

Figure 2:
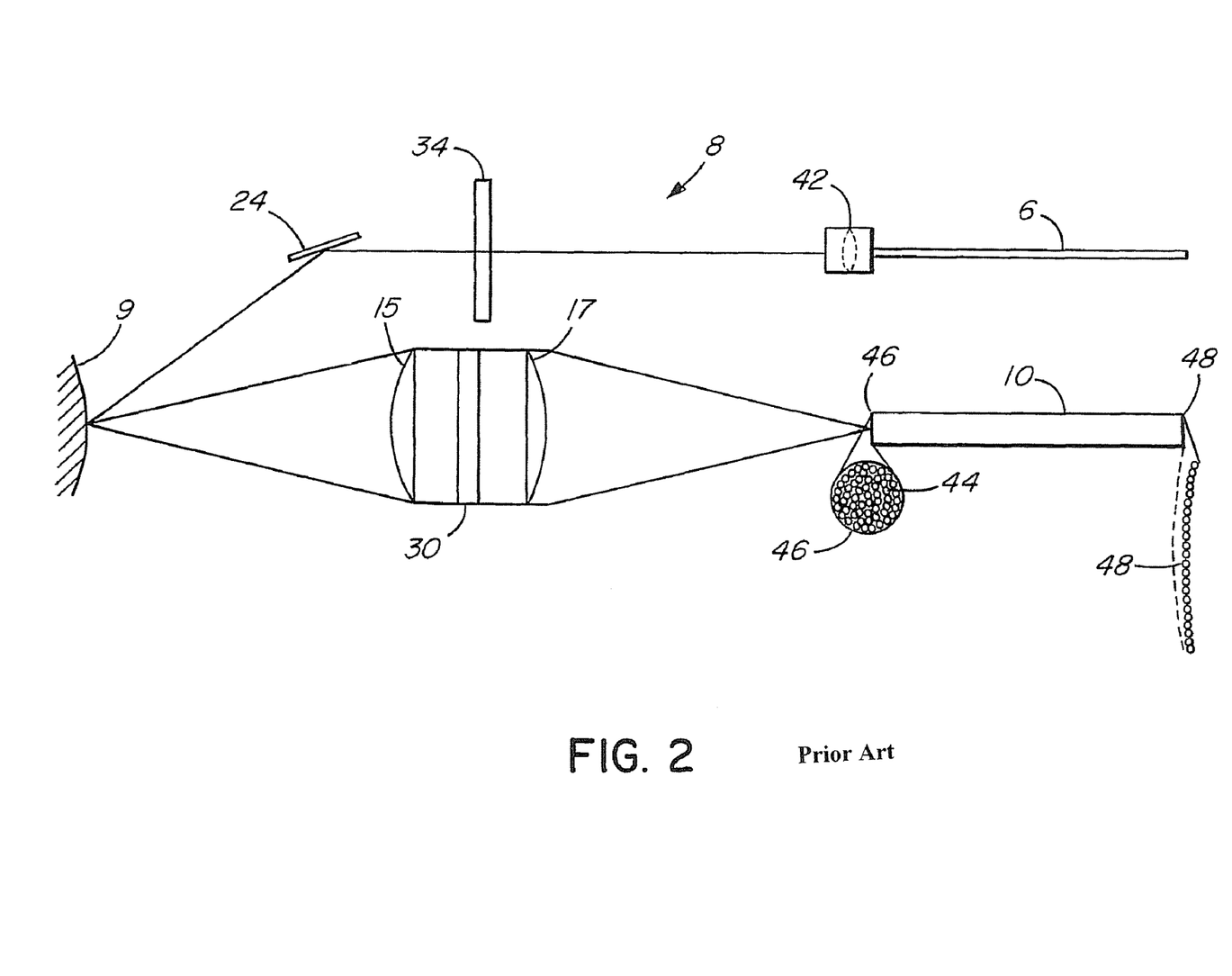
FIG. 2 is a schematic block diagram of the probe of the rapid Raman spectrometer system of FIG. 1.

This Raman probe 8 was designed to maximize the collection of tissue Raman signals while reducing the interference of Rayleigh scattered light, fiber fluorescence, and silica Raman signals. The probe 8 as illustrated in FIG. 2 consisted of two arms. An illumination arm 6 incorporated a collimating lens 42, band-pass filter (785±2.5 nm) 34, and focusing lens 24, delivering the laser light onto the skin surface 9 with a spot size of 3.5 mm. A collection arm comprising a fiber bundle 10 with collimating lens 15 and refocusing lens 17 and a holographic notch plus filter 30 (OD>6.0 at 785 nm, Kaiser) was used for collecting Raman emissions. To enhance the detection of the inherently weak Raman signals, we packed as many fibers 44 into the fiber bundle 10 as allowed by the CCD height (6.9 mm). The fiber bundle 10 consists of 58×100-μm fibers arranged in a circular shape at the input end 46 of the probe 8 and a linear array at the output end 48 which was connected to the spectrograph's entrance. Another 50-μm fiber was placed at the centre of the output linear array and split out of the bundle to terminate with a SMA connector for wavelength calibration. At the circular end 46 the fibers were packed into a 1.6 mm diameter area, which also defined the measurement spot size at the skin surface 9.

Figure 3A:
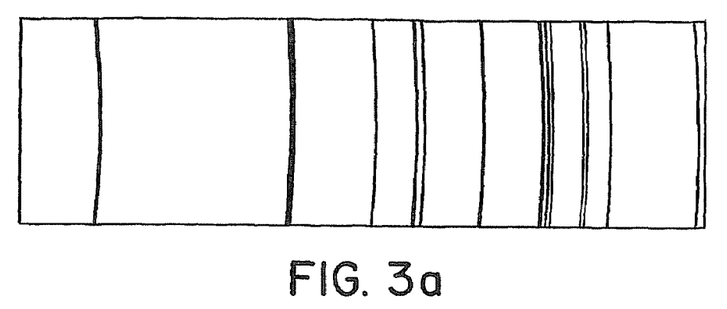
FIG. 3a is an image of a 100 μm slit on a CCD through a spectrograph, showing image aberration.
Figure 4:
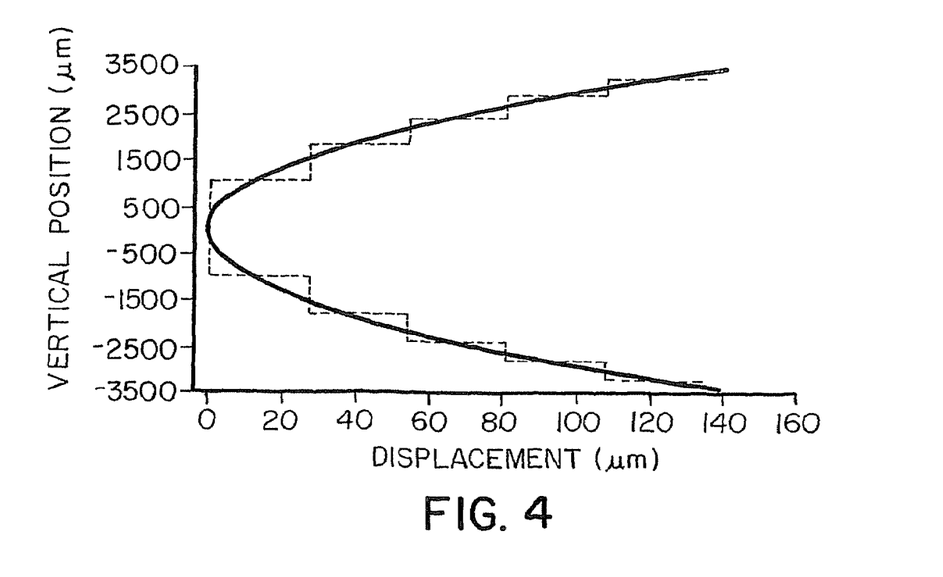

It is well known that the image of a straight slit through any spectrograph utilizing a plane grating has a curved line shape that is usually parabolic. This image aberration arises from the fact that rays from different positions along the length of the slit are incident on the grating at varying degrees of obliqueness. For spectrographs with short focal lengths, this obliqueness causes significant distortion that can affect the measurement performance of the detector. FIG. 3a shows the image aberration of a 100-μm slit through the spectrograph in an uncorrected system when illuminated by an Hg—Ar lamp. The curvature of the spectral lines is apparent, and in FIG. 4 the horizontal displacement of a spectral line from FIG. 3a is shown graphically with the displacement rounded to pixels (dashed line). The maximum horizontal displacement is five pixels (135 μm). The solid line is a linear regression-fitted parabolic curve described by $$x = 1.1904E-5y^2 + 1.19455E-4y - 0.98613 \qquad \text{Eq. 1}$$

where x is the horizontal displacement at a vertical position, y.

This image aberration causes two problems to hardware binning of CCD columns: (1) it decreases the spectral resolution; and (2) it decreases the S/N ratio achievable otherwise. It also causes problems with wavelength calibration. "Hardware binning" is CCD binning performed before signal read-out by the preamplifier. For signal levels that are readout noise limited such as for weak Raman signal measurements, hardware binning improves S/N linearly with the number of pixels grouped together. Binning can also be done using software after the signal is read out. However, "software binning" improves the S/N only by as much as the square root of the number of pixels added together. Hence, complete hardware binning of the entire vertical line is preferable for maximizing S/N. Prior to our work there has been no effort reported for correcting this image aberration. The manufacturer (Kaiser) of the HoloSpec spectrograph 2 of FIG. 1, which was used in obtaining the spectra of FIG. 3a, suggested binning the 11 segments shown in FIG. 4 separately using hardware binning and then shifting the appropriate number of pixels before summing them together using software. We call this a "combined hardware and software binning procedure". Another method is to acquire the whole image first and then add all the pixels along the curved line together by software. We call this "complete software binning procedure."

Figure 3B:
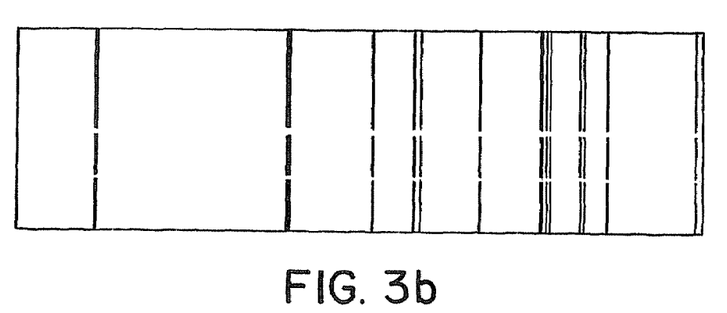

We conceived a simple but novel solution for dealing with this image aberration: a round-to-parabolic linear array. We aligned the 58×100-μm fibers of the fiber bundle 10 at the spectrograph end 48 along a curved line formed by laser drilling of a stainless steel cylinder piece, the shape of which directly corresponded to the horizontal displacement shown in FIG. 4 but in the reverse orientation. FIG. 3b shows the CCD image of the fiber bundle 10 illuminated by an Hg—Ar lamp. The central dark spots in the spectral lines are from the calibration fiber that was not illuminated. Using this specific fiber arrangement, the spectral lines are substantially straight, indicating effective image aberration correction that in turn allows us to completely bin the entire CCD vertical line (256 pixels) without losing resolution and reducing S/N. Therefore the S/N improvement we achieve with our system could be up to a maximum value of $11/\sqrt{11} = \sqrt{11} = 3.3$ times when compared to the combined hardware and software binning procedure, and $256/\sqrt{256} = \sqrt{256} = 16$ times compared to the complete software binning.

The in vivo skin Raman measurements using the '948 system under hardware binning mode can be obtained in less than 1 second, and some Raman peaks are discernible even with an exposure time of 0.01 seconds. The illumination power density is 1.56 W/cm$^2$, less than the ANSI maximum permissible skin exposure limit of 1.63 W/cm$^2$ for a 785-nm laser beam. A shutter was mounted at the laser output port and was synchronized with spectral data acquisition to make sure that the skin was only exposed to the laser light during the CCD exposure period.

Figure 5A:
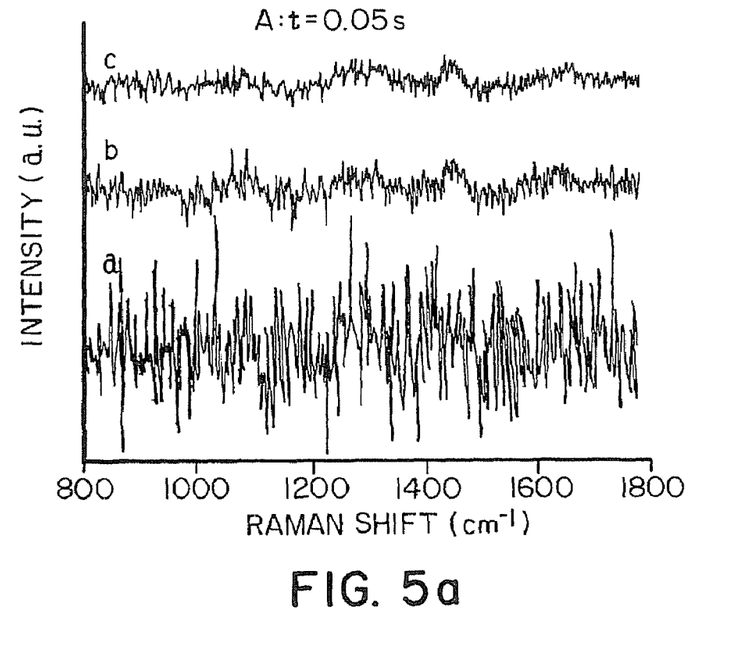
FIG. 5a is Raman spectra of healthy palm skin in three acquisition modes at a CCD exposure time of 0.05 seconds: spectrum a is from complete software binning mode; spectrum b is from combined hardware and software binning mode; and spectrum c is from complete hardware binning mode.
Figure 5B:
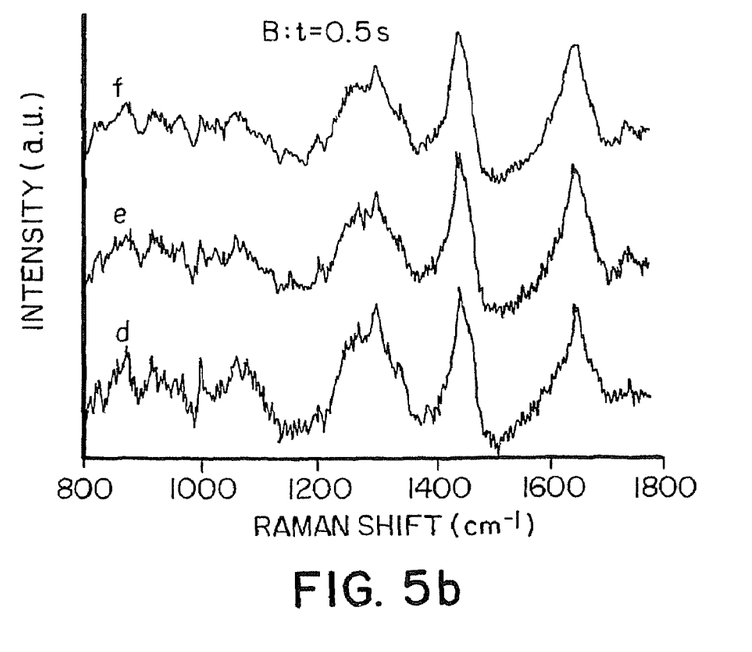
FIG. 5b is Raman spectra of healthy palm skin in three acquisition modes at a CCD exposure time of 0.5 seconds: spectrum a is from complete software binning mode; spectrum b is from combined hardware and software binning mode; and spectrum c is from complete hardware binning mode.

FIGS. 5a and 5b shows Raman spectra from a palm at a CCD exposure time of 0.05 seconds (FIG. 5a) and 0.5 seconds (FIG. 5b). The spectra were obtained under complete software binning (spectra a and d), combined hardware and software binning (spectra b and e), and complete hardware binning (spectra c and f) acquisition modes. In both FIGS. 5a and 5b, the S/N ratios of the spectra using hardware binning are better than that of the combined hardware and software binning and are much better than that of complete software binning. Please note the Raman peak at 1745 cm$^{-1}$ (from the C=O stretching band of lipid ester carbonyl) is barely visible on curve d, but appeared as a noisy small peak on curve e, whereas on curve f (obtained by our rapid Raman system) it appears as a smooth peak with great confidence.

Figure 6:
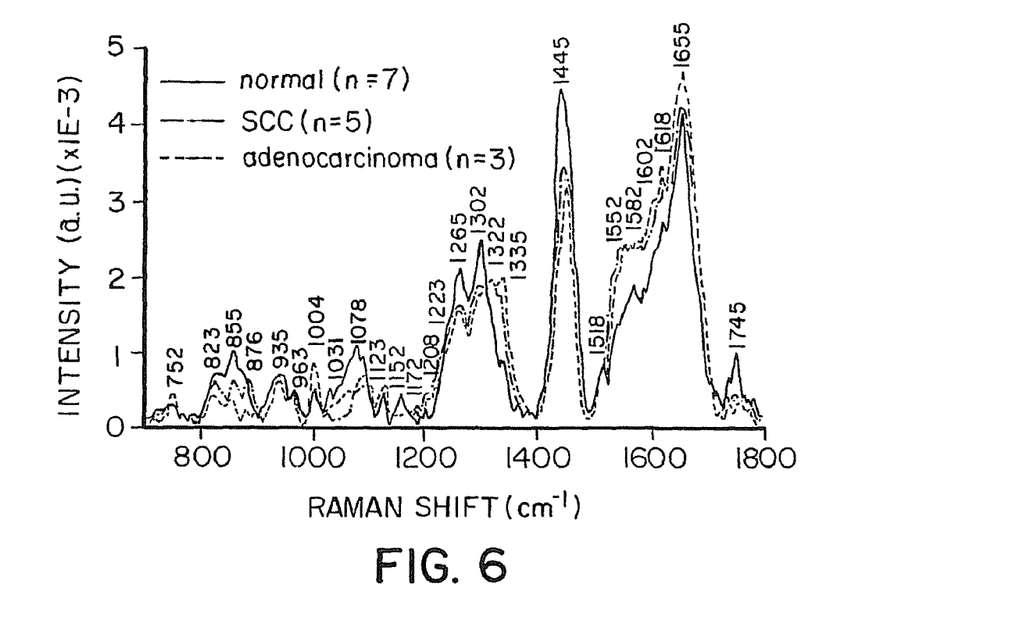
FIG. 6 is mean Raman spectra of normal and malignant (adenocarcinoma and squamous cell carcinoma) bronchial tissues.

Using the above rapid Raman system, we have measured Raman spectra on fresh normal and malignant lung tissue biopsies. The results demonstrated consistent spectral difference between normal and cancerous tissues. FIG. 6 shows the mean Raman spectra of normal and malignant (adenocarcinoma and squamous cell carcinoma) bronchial tissues. Each of the Raman spectra was normalized to the integration area under the curve to correct for variations in absolute spectral intensity.

It can be seen that while significant Raman spectral differences exist between normal and tumor tissue, Raman spectra of adenocarcinoma are very similar to those of squamous cell carcinoma with slight differences in the relative intensities of the 1335, 1445 and 1655 cm$^{-1}$ bands. Primary Raman peaks at 752, 823, 855, 876, 935, 1004, 1078, 1123, 1152, 1172, 1208, 1265, 1302, 1445, 1518, 1582, 1618, 1655, and 1745 cm$^{-1}$ can be consistently observed in both normal and tumor tissues, with the strongest signals at 1265, 1302, 1445 and 1655 cm$^{-1}$. The intensities of Raman peaks at 855, 1078, 1265, 1302, 1445, and 1745 cm$^{-1}$ in normal tissue are greater than those of tumor tissue, while Raman bands at 752, 1004, 1223, 1335 and 1550-1620 cm$^{-1}$ are more intense in tumor tissue.

Besides the intensity differences between normal and tumor tissue, the spectral shape differences were also apparent in the 1000-1100, 1200-1400, and 1500-1700 cm$^{-1}$ regions. Raman signals from 1200-1400 and 1500-1700 cm$^{-1}$ were broader in tumor tissue as compared to normal tissue, and Raman peaks at 1322 and 1335 cm$^{-1}$ were much enhanced in tumor tissue. In addition, the peak positions at 1078 and 1265 cm$^{-1}$ in normal tissue appeared to have shifted to 1088 and 1260 cm$^{-1}$ in tumor tissue, respectively.

Figure 7:
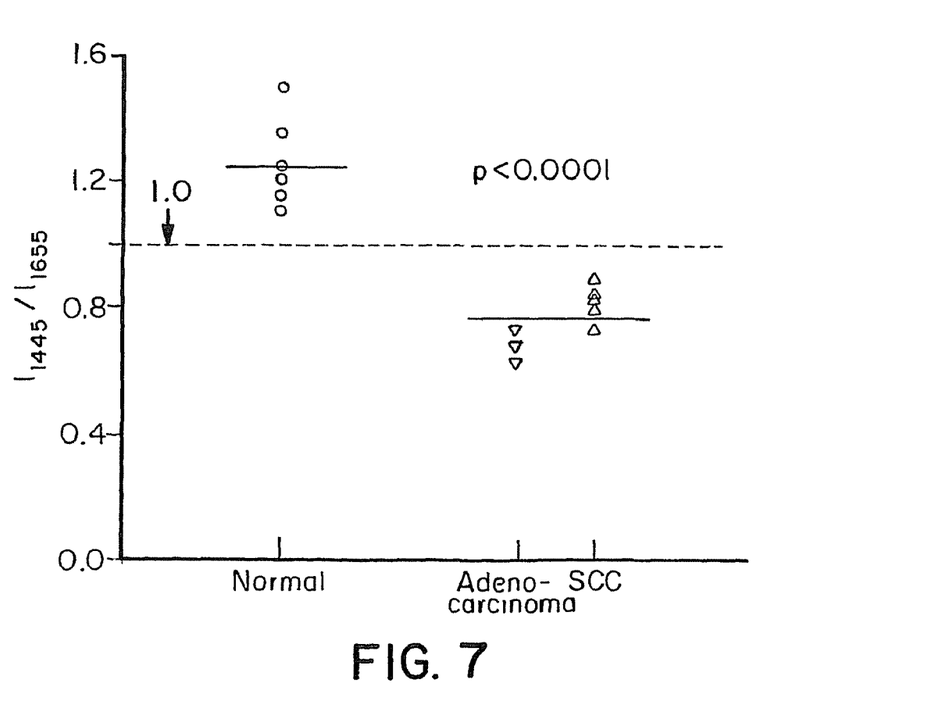
FIG. 7 is a graph of the scatter plot of the ratio of intensities of Raman spectra at 1445 $cm^{-1}$ to that at 1655 $cm^{-1}$ with respect to diagnosis.

FIG. 7 shows the scatter plot of the ratio of intensities at 1445 cm$^{-1}$ to that at 1655 cm$^{-1}$ with respect to pathological results. One notes that the peak intensity at 1655 cm$^{-1}$ is higher than that at 1445 cm$^{-1}$ in tumor tissue. In contrast, the band intensity at 1445 cm$^{-1}$ is stronger than that at 1655 cm$^{-1}$ in normal tissue. The mean ratio value (1.25±0.05, n=7) of normal tissue is significantly different from the mean ratio value (0.77±0.03, n=8) of malignant tumor (adenocarcinoma+SCC) tissue (unpaired Student's t-test, p<0.0001). The decision line ($I_{1445}/I_{1655}=1$) completely separates tumor tissue from normal tissue without any overlaps.

Assignment of the various Raman bands observed in FIG. 6 is shown in Table 1. From these assignments, the measured Raman spectra suggest that lung tumors have increased nucleic acid, tryptophan, phenylalanine content and decreased phospholipids, proline, and valine content than normal tissue. Further analysis of these spectra also suggests that proteins in normal tissue are more in the α-helical confirmation, while in malignant tissue, some proteins were involved in the β-pleated sheet or random coil configurations. The results of these preliminary data indicate that NIR Raman spectroscopy provides a significant potential for the non-invasive diagnosis of lung cancers and warranty the development of an endoscopic Raman probe for in vivo applications.

TABLE 1

Peak positions and tentative assignments of major vibrational bands observed in normal and tumor bronchial tissue.

| PEAK POSITION (cm$^{-1}$) | PROTEIN ASSIGNMENTS | LIPID ASSIGNMENTS | OTHERS |
|---|---|---|---|
| 1745w | | ν (C=O), phospholipids | |
| 1655vs | ν (C=O) amide I, α-helix, collagen, elastin | | |
| 1618s (sh) | ν (C=C), tryptophan | | ν (C=C), porphyrin |
| 1602ms (sh) | δ (C=C), phenylalanine | | |
| 1582ms (sh) | δ (C=C), phenylalanine | | |
| 1552ms (sh) | ν (C=C), tryptophan | | ν (C=C), porphyrin |
| 1518w | | | ν (C=C), carotenoid |
| 1445vs | δ (CH$_2$), δ (CH$_3$), collagen | δ (CH$_2$) scissoring, phospholipids | |
| 1335s (sh) | CH$_3$CH$_2$ wagging, collagen | | CH$_3$CH$_2$ wagging nucleic acids |
| 1322s | CH$_3$CH$_2$ twisting, collagen | | |
| 1302vs | δ (CH$_2$) twisting, wagging, collagen | δ (CH$_2$) twisting, wagging, phospholipids | |
| 1265s (sh) | ν (CN), δ (NH) amide III, α-helix, collagen, tryptophan | | |
| 1223mw (sh) | | | ν$_{as}$(PO$_2^-$), nucleic acids |
| 1208w (sh) | ν (C—C$_6$H$_5$), tryptophan, phenylalanine | | |
| 1172vw | δ (C—H), tyrosine | | |
| 1152w | ν (C—N), proteins | | ν (C—C), carotenoid |
| 1123w | ν (C—N), proteins | | |
| 1078ms | | ν (C—C) or ν (C—O), phospholipids | |
| 1031 mw (sh) | δ (C—H), phenylalanine | | |
| 1004ms | ν$_s$ (C—C), symmetric ring breathing, phenylalanine | | |
| 963w | Unassigned | | |
| 935w | ν (C—C), α-helix, proline, valine | | |
| 876w (sh) | ν (C—C), hydroxyproline | | |
| 855ms | ν (C—C), proline δ (CCH) ring breathing, tyrosine | | Polysaccharide |
| 823w | out-of-plane ring breathing, tyrosine | | |
| 752w | symmetric breathing, tryptophan | | |

Note:
ν, stretching mode;
ν$_s$, symmetric stretch;
ν$_{as}$, asymmetric stretch;
δ, bending mode;
v = very;
s = strong;
m = medium;
w = weak;
sh = shoulder.

For successful in vivo Raman spectral measurement through the endoscope, the key specifications of the endoscopic laser-Raman probe are:
1. Be small enough to pass through the instrument channel (2.2 mm size) of the endoscope;
2. Incorporate proper filtering mechanism to minimize or eliminate the background Raman and fluorescence signals generated from the fiber-optic material; and
3. Be able to collect enough signal so that a Raman spectrum can be acquired in seconds or sub-seconds.

To preserve the high S/N ratio advantage of the skin Raman probe described in the '948 patent, the present invention utilizes a two-step filtering strategy for the endoscopic Raman probe: (1) first-order filtering at the tip of the fiber bundle and (2) high-performance filtering at the entrance point of the instrument channel of the endoscope.

Figure 8:
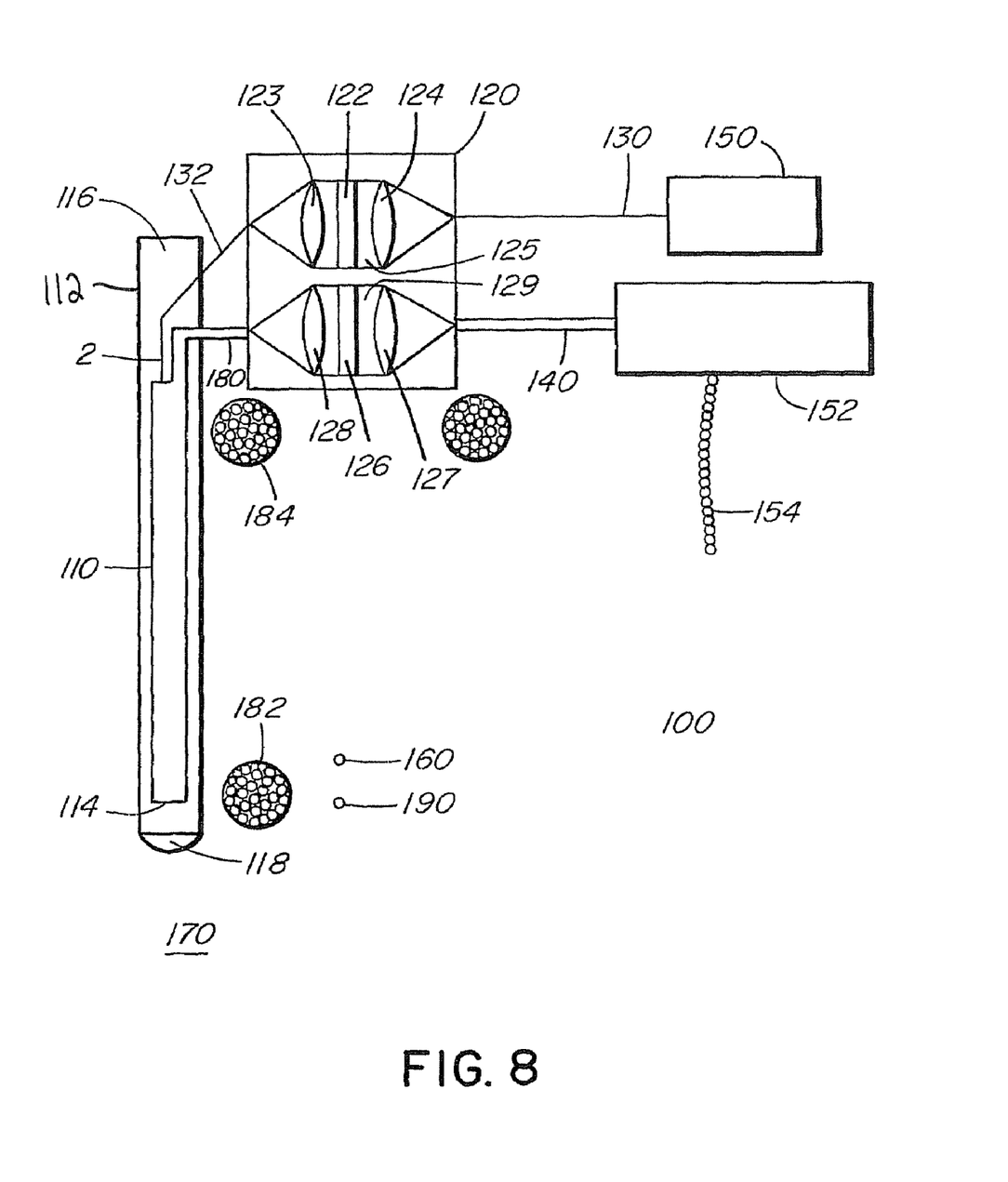
FIG. 8 is schematic diagram of the in vivo Raman endoscopic probe of the present invention.

FIG. 8 shows the schematics of the preferred embodiment of the endoscopic Raman probe system 100 of the present invention. It consists of a probing fiber bundle assembly 110, a filter adapter 120, an illumination fiber 130, and a round-to-parabolic linear array fiber bundle 140. The illumination light from the diode laser 150 is focused into the illumination fiber 130, which is connected to the filter adapter 120 close to the entrance of the instrument channel of the bronchoscope 116. The illumination light is chosen to be at a wavelength as close as possible that will excite the molecules of interest. In the preferred embodiment, laser light at 785 nm meets this objective for detection of lung cancer. Other wavelengths can be chosen depending on the properties of the molecules of interest.

A high-performance BP filter (in the preferred embodiment, 785±2.5 nm) 122 passes through the laser light and filters out the background Raman and fluorescence signals generated inside the illumination fiber 130 between the diode laser 150 and the filter adapter 120. The filtered laser light is refocused into the illumination fiber 132 in the probing fiber bundle assembly 110. Because this part of the illumination fiber 132 is short, the generated background Raman and fluorescence from the fiber is small. Nevertheless, the distal end 114 of the illumination fiber 132 is coated with a SP filter 160 to further reduce these background signals. The induced Raman signal from the tissue 170 is picked up by collection fibers 180 in the probing fiber bundle assembly 110. LP filter coatings 190 are applied to the distal end of these fibers 180 to block the back-scattered laser light from entering the probe 110. At the proximal end 112 of the probing fiber bundle assembly 110, these collection fibers 180 are packed into a round bundle 184 and connected to the filter adapter 120. A notch filter (in the preferred embodiment, OD>6.0 at 785 nm, Kaiser) 126 is used to further block the laser wavelengths and allow the Raman signals to pass through. The Raman signals are refocused by a focusing lens 127 into the round-to-parabolic linear array fiber bundle 140. At the entrance of the spectrometer 152, these collection fibers 140 are aligned along a parabolic line 154 to correct for image aberration of the spectrograph to achieve better spectral resolution and higher S/N ratio in a fashion similar to the skin Raman probe described in the '948 patent.

To preserve the high S/N ratio advantage achieved in the skin Raman probe work described in the '948 patent, the probing fiber bundle assembly 110 of the preferred embodiment will consist of 58 100-μm collection fibers 180 and a 200-μm illumination fiber 132. These fibers are preferably low-OH fused silica type with N.A.=0.22. The bifurcated assembly 110 has a diameter of 1.9 mm and a length of 65 cm to feed through the instrument channel of an endoscope 116, preferably an Olympus BF-20 or BF-40 bronchoscope. This assembly 110 is kept as short as possible to reduce background Raman and fluorescence signals from the fiber material. It is just about two cm longer than the length of the instrument channel.

At the distal common end 114, the illumination fiber 132 is located at the centre of the bundle 182 and its end is coated (such as coatings made by LightMatrix Technologies, Inc.) to generate a SP filter 160 with a cut-off wavelength, in the preferred embodiment, of around 825 nm. The collection fibers 180 are arranged around the illumination fiber 132 and their ends are coated to generate a LP filter 190 with a cut-off wavelength, in the preferred embodiment, of around 825 nm. Alternatively, more advanced technologies, e.g. fiber-Bragg gratings, may be used. At the proximal end 112, the assembly 110 is branched out into a single illumination fiber 132 and a collection fiber bundle 184 (circular shape) to be connected to the filter adapter 120. In the assembly 110, the illumination fiber 132 is metal coated for optical isolation to prevent cross-talks with collection fibers 180.

The filter specifications described and utilized are dependent upon the laser wavelength used and are described for the preferred embodiment. Generally, if the laser wavelength is $\lambda_0$, the BP filter should pass light of $\lambda_0 \pm \Delta\lambda$. The cut-off wavelength for LP and SP filters is $\lambda_0 + \Delta\lambda_1$. In the preferred embodiment, $\lambda_0$=785 nm, $\Delta\lambda$=2.5 nm and $\Delta\lambda_1$=40 nm.

So, in the preferred embodiment, the BP filter 122 passes light between 782.5 and 787.5 nm, thereby isolating the illumination light from the laser 150 to the illumination fiber 132 at 785 nm. This illumination light then pass through a SP filter 160 with a cut-off of 825 nm, to pass light shorter than this wavelength and attenuate longer wavelengths, to further ensure that no illumination light exists in the signal range above 825 nm. The illumination light then encounters the subject 170 and induces Raman scattering. The Raman-scattered light enters the collection fibers 180 after first passing through the LP filter 190 with a cut-off of 825, pass light above this wavelength and attenuate shorter wavelengths, to ensure that no non-specific light, such as would result from reflection from the laser illumination light or non-Raman-scattered light, will enter the measurement system. The notch filter 126 then further ensures that no laser light proceeds into the spectrometer 152.

When performing endoscopic Raman measurements, the distal end 114 of the endoscope 116 is in gentle contact with the tissue surface 170. A quartz window 118 (or other materials with low Raman and fluorescence background) may be attached to the end of the probe 116 to keep the probe 116 at a fixed distance from the tissue surface 170. When the probe 116 is moved away from the tissue surface 170, the sampling depth will change. Pulling the probe 116 away from the tissue surface 170 will increase the overlap between the illumination area and the collection area; therefore, it may increase the Raman signals collected. Theoretical modeling (Monte Carlo simulation) and experimental testing will be combined to optimize the distance (i.e. the thickness of the window) between the probe 116 and the tissue surface 170.

The filter adapter 120 will consist of two identical pre-aligned filter holders 125 and 129, preferably from OZ Optics Ltd. (Carp, ON, Canada). The OZ Optics filter holder 125 consists of a collimating lens 124 to collimate the light beam from the illumination fiber 130 before incident on the BP filter 122 and a refocusing lens 123 to focus the filtered beam onto the illumination fiber 132 in the fiber bundle assembly 110. The filter holder 129 consists of a collimating lens 128 to collimate the light from the collection fibers 180 before incident on the notch filter 126 and a refocusing lens 127 to focus the filtered light into the round-to-parabolic linear array 140. The single fiber 132 and fiber bundle 180 are connected to the filter adapter 120 by SMA connectors. A holder will attach the filter adapter 120 to the bronchoscope 116.

The fiber bundle 110 consists of 58 100-μm fibers. It is packed into circular shape and terminated with an SMA connector to the filter adapter 120. At the spectrometer 152 end, the 58 fibers are aligned along a curve 154 formed by laser drilling of a stainless steel cylinder piece, the shape of which corresponds directly to the horizontal displacement shown in FIG. 4 and expressed as a parabolic curve in Eq. (1) above. This curve serves to correct for image aberration of the spectrograph 52 to achieve better spectral resolution and higher S/N ratio in a fashion similar to the skin Raman probe described in the '948 patent.

The probing fiber bundle assembly 110, the filter adapter 120, the laser light source 150 and illumination fiber 130, 32, the round-to-parabolic linear array 140, and the spectrometer 152 are integrated to form the endoscopic Raman probe system 100.

While a preferred embodiment of the present invention is shown and described, it is envisioned that those skilled in the art may devise various modifications of the present invention without departing from the spirit and scope of the appended claims.

I claim:

1. An in vivo Raman endoscope comprising:
   a probing fiber bundle having a distal end and a proximal end and comprising at least one illumination fiber and a plurality of collection fibers,
   a short-pass filter on the distal end of said at least one illumination fiber,
   a long-pass filter on the distal end of said plurality of collection fibers,
   a filter adapter on the proximal end of said fiber bundle, comprising a band-pass filter in optical communication with said illumination fiber and a notch filter in optical communication with said plurality of collection fibers, and
   a round-to-parabolic linear array fiber bundle in optical communication with said plurality of collection fibers through said notch filter.

2. The endoscope of claim 1, wherein said short-pass filter comprises a coating on the distal end of said at least one illumination fiber.

3. The endoscope of claim 2, wherein said short-pass filter has a cut-off wavelength of about 825 nm.

4. The endoscope of claim 1, wherein said long-pass filter comprises a coating on the distal end of said plurality of collection fibers.

5. The endoscope of claim 4, wherein said long-pass filter has a cut-off wavelength of about 825 nm.

6. The endoscope of claim 4, wherein said short-pass filter comprises a coating on the distal end of said at least one illumination fiber.

7. The endoscope of claim 6, wherein said short-pass filter has a cut-off wavelength of about 825 nm and said long-pass filter has a cut-off wavelength of about 825 nm.

8. The endoscope of claim 1, wherein said band-pass filter transmits in a range around 785 nm.

9. The endoscope of claim 8, wherein said range is plus-or-minus 2.5 nm.

10. The endoscope of claim 1, wherein said notch filter has an optical density greater than 6.0 at 785 nm.

11. The endoscope of claim 1, further comprising means for delivering illumination light to said filter adapter and wherein said filter adapter further comprises a collimating lens between said means for delivering and said band-pass filter.

12. The endoscope of claim 11, wherein said means for delivering comprises a laser.

13. The endoscope of claim 11, further comprising a focusing lens between said band-pass filter and said at least one illumination fiber.

14. The endoscope of claim 11, wherein said illumination light is chosen at a wavelength to induce Raman scattering.

15. The endoscope of claim 14, wherein said illumination light is monochromatic.

16. The endoscope of claim 15, wherein said means for delivering illumination light is a laser.

17. The endoscope of claim 16, wherein said laser is a diode laser.

18. The endoscope of claim 17, wherein said illumination light is about 785 nm.

19. The endoscope of claim 1, wherein said filter adapter further comprises a collimating lens between said plurality of collection fibers and said notch filter.

20. The endoscope of claim 19, further comprising a focusing lens between said notch filter and said round-to-parabolic linear array fiber bundle.

21. The endoscope of claim 1, further comprising means for delivering illumination light to said filter adapter and said filter adapter further comprises a collimating lens between said means for delivering and said band-pass filter a focusing lens between said band-pass filter and said at least one illumination fiber, a collimating lens between said plurality of collection fibers and said notch filter, and a focusing lens between said notch filter and said round-to-parabolic linear array fiber bundle.

22. The endoscope of claim 1, further comprising a quartz window at the distal end of said fiber bundle.

23. The endoscope of claim 1, further comprising:
   a spectrometer in optical communication with said plurality of collection fibers through said notch filter.

24. The endoscope of claim 23, wherein the number and core diameter of said plurality of collection fibers are selected to fill the vertical height of a detector of said spectrometer.

25. The endoscope of claim 24, wherein said detector is a CCD.

26. The endoscope of claim 1, wherein said illumination fiber is metal coated.

27. An apparatus for in vivo Raman spectral measurements of a tissue, comprising:
   an endoscope;
   a light source generating illumination light, said illumination light inducing a Raman signal from the tissue;
   a filter adapter receiving said illumination light from said light source;
   a fiber bundle assembly having a distal end and a proximal end, said fiber bundle assembly configured to pass through an instrument channel of said endoscope, said instrument channel having an entrance at a proximal end of said endoscope, said filter adapter being connected to said fiber bundle assembly close to said entrance of said instrument channel, said fiber bundle assembly comprising an illumination fiber and a plurality of collection fibers, said illumination fiber receiving said illumination light from said filter adapter, said plurality of collection fibers receiving a Raman signal from the tissue and said filter adapter receiving said Raman signal from said plurality of collection fibers, said filter adapter comprising a band-pass filter for said illumination light and a notch filter for said Raman signal;
a first-order filter on said distal end of said fiber bundle assembly, said first-order filter comprising a short-pass filter on said illumination fiber and a long-pass filter on said plurality of collection fibers; and
a round-to-parabolic linear array receiving said Raman signal from said filter adapter.

28. The apparatus of claim 27, wherein said short-pass filter comprises a coating on the distal end of said illumination fiber.

29. The apparatus of claim 27, wherein said short-pass filter has a cut-off wavelength of about 825 nm.

30. The apparatus of claim 27, wherein said long-pass filter comprises a coating on the distal end of said plurality of collection fibers.

31. The apparatus of claim 30, wherein said short-pass filter comprises a coating on the distal end of said illumination fiber.

32. The apparatus system of claim 31, wherein said short-pass filter has a cut-off wavelength of about 825 nm and said long-pass filter has a cut-off wavelength of about 825 nm.

33. The apparatus of claim 27, wherein said long-pass filter has a cut-off wavelength of about 825 nm.

34. The apparatus of claim 27, wherein said band-pass filter transmits in a range around 785 nm.

35. The apparatus of claim 34, wherein said range is plus-or-minus 2.5 nm.

36. The apparatus of claim 27, wherein said notch filter has an optical density greater than 6.0 at 785 nm.

37. The apparatus of claim 27, wherein said filter adapter further comprises a collimating lens between said light source and said band-pass filter.

38. The apparatus of claim 37, wherein said light source comprises a laser.

39. The apparatus of claim 37, further comprising a focusing lens between said band-pass filter and said illumination fiber.

40. The apparatus of claim 27, wherein said filter adapter further comprises a collimating lens between said plurality of collection fibers and said notch filter.

41. The apparatus of claim 40, further comprising a focusing lens between said notch filter and said round-to-parabolic linear array.

42. The apparatus of claim 27, wherein said filter adapter further comprises a collimating lens between said light source and said band-pass filter, a focusing lens between said band-pass filter and said illumination fiber, a collimating lens between said plurality of collection fibers and said notch filter, and a focusing lens between said notch filter and said round-to-parabolic linear array.

43. The apparatus of claim 27, further comprising a quartz window at the distal end of said fiber bundle assembly.

44. The apparatus of claim 27, wherein said illumination light is monochromatic.

45. The apparatus of claim 44, wherein said light source is a laser.

46. The apparatus of claim 45, wherein said laser is a diode laser.

47. The apparatus of claim 46, wherein said illumination light is about 785 nm.

48. The apparatus of claim 27, further comprising a spectrometer receiving said Raman signal from said plurality of collection fibers through said notch filter.

49. The apparatus of claim 48, wherein the number and core diameter of said plurality of collection fibers are selected to fill the vertical height of a detector of said spectrometer.

50. The apparatus of claim 49, wherein said detector is a CCD.

51. The apparatus of claim 27, wherein said illumination fiber is metal coated.

52. An apparatus for in vivo Raman spectral measurements, comprising:
an endoscope;
a light source;
a filter adapter connected to said light source;
a fiber bundle assembly configured to pass through an instrument channel of said endoscope, said instrument channel having an entrance at a proximal end of said endoscope, said fiber bundle assembly comprising an illumination fiber and a plurality of collection fibers, said filter adapter comprising a band-pass filter for said illumination fiber and a notch filter for said plurality of collection fibers, said fiber bundle assembly having a distal end and a proximal end, said filter adapter being connected to said proximal end of said fiber bundle assembly at said entrance of said instrument channel;
a filter at said distal end of said fiber bundle assembly, said filter comprising a short-pass filter on a tip of said illumination fiber and a long-pass filter on distal tips of said plurality of collection fibers; and
a round-to-parabolic linear array connected to said filter adapter.

53. The apparatus of claim 52, wherein said short-pass filter comprises a coating on said illumination fiber.

54. The apparatus of claim 52, wherein said short-pass filter has a cut-off wavelength of about 825 nm.

55. The apparatus of claim 52, wherein said long-pass filter comprises a coating on said plurality of collection fibers.

56. The apparatus of claim 55, wherein said short-pass filter comprises a coating on said illumination fiber.

57. The apparatus of claim 56, wherein said short-pass filter has a cut-off wavelength of about 825 nm and said long-pass filter has a cut-off wavelength of about 825 nm.

58. The apparatus of claim 52, wherein said long-pass filter has a cut-off wavelength of about 825 nm.

59. The apparatus of claim 52, wherein said band-pass filter transmits in a range around 785 nm.

60. The apparatus of claim 59, wherein said range is plus-or-minus 2.5 nm.

61. The apparatus of claim 52, wherein said notch filter has an optical density greater than 6.0 at 785 nm.

62. The apparatus of claim 52, wherein said light source comprises a laser.

63. The apparatus of claim 62, wherein said laser is a diode laser.

64. The apparatus of claim 52, further comprising a spectrometer connected to said filter adapter.

65. The apparatus of claim 64, wherein the number and core diameter of said plurality of collection fibers are selected to fill the vertical height of a detector of said spectrometer.

66. The apparatus of claim 65, wherein said detector is a CCD.

67. The apparatus of claim 52, wherein said illumination fiber is metal coated.

* * * * *

UNITED STATES PATENT AND TRADEMARK OFFICE
CERTIFICATE OF CORRECTION

PATENT NO. : 7,383,077 B2
APPLICATION NO. : 10/761703
DATED : June 3, 2008
INVENTOR(S) : Haishan Zeng

It is certified that error appears in the above-identified patent and that said Letters Patent is hereby corrected as shown below:

Column 1, Line 32 "thick and LIP" should be -- thick and up --

Column 3, Line 46 "iii vivo" should be -- in vivo --

Signed and Sealed this

Thirtieth Day of September, 2008

JON W. DUDAS
*Director of the United States Patent and Trademark Office*